United States Patent
Cangelosi

[11] Patent Number: 5,997,567
[45] Date of Patent: Dec. 7, 1999

[54] FORKED SUTURE FORCEPS

[76] Inventor: Joseph Cangelosi, 8646 Butte Cir., #607-C, Huntington Beach, Calif. 92646

[21] Appl. No.: 09/037,667

[22] Filed: Mar. 10, 1998

[51] Int. Cl.[6] .................................................. A61B 17/28
[52] U.S. Cl. .......................................... 606/210; 294/99.2
[58] Field of Search .................... 606/210, 211, 606/205, 206, 207; 294/99.2

[56] References Cited

U.S. PATENT DOCUMENTS

| | | | |
|---|---|---|---|
| 574,476 | 1/1897 | Coy | 294/99.2 |
| 629,082 | 7/1899 | Law | 294/99.2 |
| 2,665,692 | 11/1954 | L'Esperance | 606/211 |
| 2,733,716 | 2/1956 | Roberts | 606/211 |
| 3,277,895 | 10/1966 | Johnson | 128/325 |
| 3,815,609 | 6/1974 | Chester | 606/210 |
| 3,889,995 | 6/1975 | Lin | 294/99.2 |
| 4,127,112 | 11/1978 | Sherlock et al. | 606/210 |
| 4,303,268 | 12/1981 | Davidson | 606/210 |
| 4,610,252 | 9/1986 | Catalano | 606/210 |
| 4,955,897 | 9/1990 | Ship | 606/210 |
| 5,047,046 | 9/1991 | Bodoia | 606/210 |
| 5,059,198 | 10/1991 | Gimpelson | 606/119 |
| 5,254,095 | 10/1993 | Harvey | 606/210 |
| 5,258,005 | 11/1993 | Christian | 606/210 |
| 5,263,968 | 11/1993 | Sorensen | 294/99.2 |
| 5,284,162 | 2/1994 | Wilk | 128/898 |
| 5,336,228 | 8/1994 | Cholhan | 606/119 |
| 5,421,721 | 6/1995 | Fyffe | 433/159 |
| 5,474,057 | 12/1995 | Makower et al. | 600/214 |
| 5,549,636 | 8/1996 | Li | 606/206 |
| 5,690,606 | 11/1997 | Slotman | 600/206 |
| 5,697,933 | 12/1997 | Gundlapalli | 606/96 |

OTHER PUBLICATIONS

Moore Medical Corp., Surgical Instruments Catalog, 2 pages—Forceps (pp. 238–239).

*Primary Examiner*—Paul J. Hirsch
*Attorney, Agent, or Firm*—Dennis Beech

[57] ABSTRACT

The forked suture forcep is a traditional forcep with handle and split planar arms; however, the arm distal ends have a two prong fork attached. The pair of prongs on each arm fork allow holding tissue taut while suturing a wound or incision. In addition the prongs and the cross member between them have graduation measures to allow accurate approximation of needle insertion points for uniform suturing along the wound or incision. This provides for properly aligning the tissue to be closed to promote faster healing and to minimize scarring.

3 Claims, 1 Drawing Sheet

FORKED SUTURE FORCEPS

BACKGROUND OF THE INVENTION

1. Field of the Invention

This invention relates to surgical instruments used to hold tissue for purposes of suturing incisions or wounds. The new device has a fork with two prongs at the distal end of each forcep arm to hold tissue at two locations simultaneously.

2. Description of Related Art

There are currently in use many shapes and styles of forceps for holding tissue as part of surgical procedures. However, these forceps have a handle with two planar arms extending therefrom. These arms are normally split and may be smooth or have teeth or serrations at the tip. The forceps are used by pinching the arms together such that the tips grip the tissue in the area in which a suturing is to be performed.

When such two arm forceps are used to hold tissue or membrane for suturing, the surgeon must move the forceps from side to side laterally across the wound while inserting the needle and therefore is required to guess distance to attempt to aline the sides of the incision to avoid wrinkling when closing. This problem exists along the longitudinal dimension of the incision as offset between sides will cause tissue to be pulled relative to the distance between stitches. Also, if needle insertions are not at the same relative distance from the edge of the tissue a pulling or twisting between stitches will occur. Both problems cause irregularities and distortions in joining the edges of the tissue which leads to slower healing and the likelihood of a noticeable scar.

The present invention adds a pair of prongs as a fork to each arm of the forceps. The prongs each have graduation measures to determine distance from the edge of the tissue being held. In addition the cross member between the prongs has graduation measures to determine the distance between stitches. The forked suture forceps thereby hold the tissue taut and allow the surgeon to measure longitudinal and lateral distance along each edge of an incision to locate needle insertion positions to align corresponding stitch points to more evenly close an incision.

SUMMARY OF THE INVENTION

One object of the present invention is to improve forceps for use in holding tissue at the location of a wound or incision for purposes of suturing or stitching the wound. Another object is to provide graduation measures on the prongs and cross member of the forcep forks to improve the approximation of needle insertion positions to align tissue properly to close an incision.

In accordance with the description presented herein, other objectives of this invention will become apparent when the description and drawings are reviewed.

DESCRIPTION OF THE PREFERRED EMBODIMENT

The forked suture forceps have the traditional handle with split planar arms; however, the arm ends have a two prong fork for holding tissue. The fork is sized to be used with the tissue or membrane to be held for suturing, i.e., delicate tissue requiring smaller, finer fork and prongs and thicker skin requiring larger, stronger fork and prongs. The forks have graduation measures on the prongs and the cross member to approximate suture insertion positions along the incision or wound to properly align tissue for closing.

Figure 1:
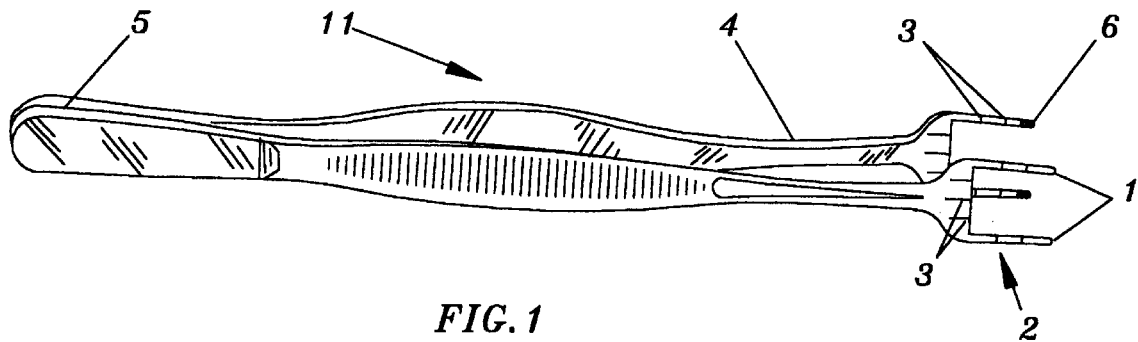
FIG. 1 illustrates a perspective view of the forked suture forceps.
Figure 2:
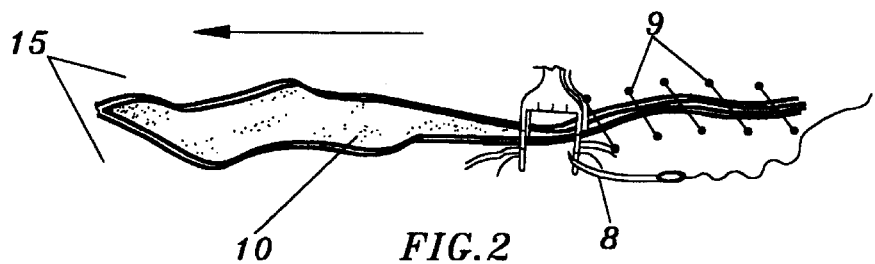
FIG. 2 illustrates a perspective view of the forks of the forceps holding tissue for suturing.
Figure 3:
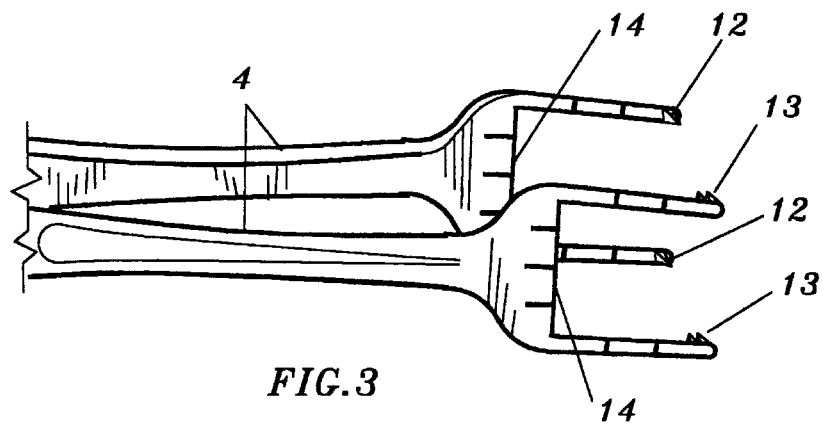
FIG. 3 illustrates a perspective view of the forks.

Referring to FIGS. 1 through 3, a forcep (11) has a handle (5) at its proximal end which is split into two planar arms (4) which arms (4) have forks (2) at the distal end. The forks (2) have a pair of prongs (1) and cross member (14). The prongs (1) at the tips (12) may have engagement edges (6) which are smooth, have serrations or have teeth (13) or protrusions depending on the type of tissue or membrane to be held during suturing.

The prongs (1) and cross member (14) have graduation measures (3) for use in determining the suture (9) locations or position along the incision (10) or wound. The prongs (1) hold the tissue (15) taut and the surgeon uses the prong (1) graduation measures (3) to approximate relative lateral distance from the edge of the incision (10) between suture (9) positions for each needle (8) insertion. Similarly the cross member (14) graduation measures (3) are used to approximate relative longitudinal spacing along the incision (10) such that opposing needle (8) insertion points across the incision (10) are aligned. As illustrated in the figures, the prongs (1) are generally straight with the cross member (14) having a straight edge at (14) to create a generally rectangular opening for flexibility in aligning the needle (8) while holding the tissue (15). This allows the user to see the area to be sutured, yet provides flexibility through use of the graduation measures (3) to place the needle (8) at the preferred point.

Use of the forceps (11) along the incision (10) as described to suture and close an incision (10) allows closer relative positioning of each suture (9) location. Use of the forks (2) and graduation measures (3) results in a practically perfect approximation of the edges of the wound or incision (10) which leads to faster healing and reduces the likelihood of a noticeable scar.

I claim:

1. A device for holding tissue along an incision, wound and the like to aid in suturing comprising:

a forceps with a handle at a proximal end and two arms attached;

a fork at a distal end of each arm wherein;

each fork having a pair of prongs generally straight in form extending approximately parallel to the forceps longitudinal axis with an engagement edge at a tip;

each fork having a cross member between and joining the prongs wherein the cross member extends laterally between the prongs and having a straight edge to create a generally rectangular open fork; and the prongs have a plurality of graduation measures and the cross member has a plurality of graduation measures for aiding in approximating suture insertion position.

2. The device as in claim 1, wherein the straigh edge of the cross member is at least one centimeter wide.

3. A method for suturing a wound with a two prong forked forceps having graduation measures on each prong and a cross member comprising the steps of:

holding the tissue taut by closing the forceps prongs on each side of the wound;

locating the proper insertion point for a needle using the graduation measures; and inserting the needle for pulling the suture through the tissue.

* * * * *